United States Patent [19]

Kodama et al.

[11] Patent Number: 5,480,888
[45] Date of Patent: Jan. 2, 1996

[54] INHIBITOR FOR RESTENOSIS AFTER PERCUTANEOUS CORONARY ARTERIOPLASTY

[75] Inventors: Kazuhisa Kodama, Takarazuka; Atsushi Hirayama, Osaka; Hiroyuki Masayasu, Tokyo, all of Japan

[73] Assignee: Daiichi Pharmaceutical Co., Ltd., Tokyo, Japan

[21] Appl. No.: 256,268

[22] PCT Filed: Jan. 14, 1993

[86] PCT No.: PCT/JP93/00045

§ 371 Date: Jul. 11, 1994

§ 102(e) Date: Jul. 11, 1994

[87] PCT Pub. No.: WO/93/13762

PCT Pub. Date: Jul. 22, 1993

[30] Foreign Application Priority Data

Jan. 17, 1992  [JP]  Japan ............. 4-006552

[51] Int. Cl.$^6$ ............. C07D 213/40; A61K 31/33; A61K 31/34; A61K 31/165
[52] U.S. Cl. ............. 514/310
[58] Field of Search ............. 514/310

[56] References Cited

U.S. PATENT DOCUMENTS 4,711,961  12/1987  Welter et al. ............. 548/121
5,187,105  2/1993  Allbarella et al. ............. 436/119

Primary Examiner—Arthur C. Prescott
Attorney, Agent, or Firm—Oblon, Spivak, McClelland, Maier, & Neustadt

[57] ABSTRACT

An inhibitor for restenosis after percutaneous coronary arterioplasty, which comprises, as an active ingredient, a compound of the following formula (1), (1') or a pharmaceutically acceptable salt thereof:

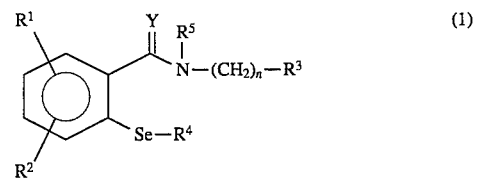

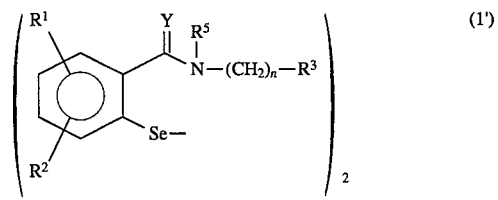

wherein $R^1$ and $R^2$ are independently a hydrogen atom, a halogen atom, a trifluoromethyl group, a nitro group, a C1–C6 alkyl group or a C1–C6 alkoxyl group, and $R^1$ and $R^2$ may be linked to form a methylenedioxy group; $R^3$ is an optionally substituted aryl group, an optionally substituted aromatic heterocyclic group, an optionally substituted 5 to 7-membered cycloalkyl or cycloalkenyl group; $R^4$ is a hydrogen atom, a hydroxyl group, an -S-glutathione residue, an -S-α-amino acid residue, or an aralkyl group optionally having substituent(s) in the aryl moiety; $R^5$ is a hydrogen atom or a C1–C6 alkyl group, and $R^4$ and $R^5$ may be linked to form a single bond; Y is an oxygen atom or a sulfur atom; n is an integer of from 0 to 5, and the selenium atom may be oxidized.

The inhibitor of the present invention exhibits excellent inhibitory effect against restenosis after PTCA with low toxicity.

2 Claims, No Drawings

5,480,888

INHIBITOR FOR RESTENOSIS AFTER PERCUTANEOUS CORONARY ARTERIOPLASTY

This application is a 371 of PCT/JP93/100045 Jan. 14, 1993.

TECHNICAL FIELD

The present invention relates to a pharmaceutical agent for inhibiting restenosis after percutaneous coronary arterioplasty (hereinafter referred to as PTCA).

BACKGROUND ART

PTCA is a relatively new approach to the treatment of ischemic heart diseases, which involves mechanical dilatation of the stenosed region of the coronary artery by balloons. However, the mechanically dilated part of the coronary arteries is known to undergo restenosis in several months after operation with a frequency of about 40%. Thus, PTCA is not a radical therapy for stenosed lesions of the coronary arteries. In order to inhibit the restenosis, antiplatelets, anticoagulants, etc. have heretofore been studied, but drugs which provide satisfactory clinical results have never been discovered.

Accordingly, there remains a need for a pharmaceutical agent which exhibits excellent inhibiting effect against restenosis after PTCA.

Compounds of the following formula (1) or (1') are known to be useful as antioxidants having glutathione peroxidase-like activity and/or lipoxigenase inhibitory activity (see, for example, Japanese Patent Application Laid-open Nos. 59-42373, 57-67568, 59-39894, 60-226868 and 61-50963, Biochemical Pharmacology, vol. 33, No. 20, 3235 to 3239 and 3241 to 3245 (1984)). However, the interrelation between these activities and the effect of inhibiting post-PTCA restenosis has remained unknown.

In view of the above, the inventors of the present invention have conducted careful studies and, as a result, have found that the compounds of the following formula (1) or (1') have an excellent effect of inhibiting restenosis after PTCA. The present invention has been accomplished based on this finding.

DISCLOSURE OF INVENTION

According to the present invention, there is provided an inhibitor for restenosis after percutaneous coronary arterioplasty, which comprises a compound of the following formula (1) or (1'), or a pharmaceutically acceptable salt thereof as an active ingredient:

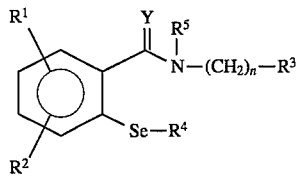

(1)

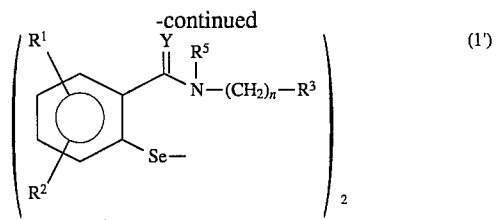

wherein $R^1$ and $R^2$ are independently a hydrogen atom, a halogen atom, a trifluoromethyl group, a nitro group, a C1–C6 alkyl group or a C1–C6 alkoxyl group, and $R^1$ and $R^2$ may be linked to form a methylenedioxy group; $R^3$ is an optionally substituted aryl group, an optionally substituted aromatic heterocyclic group, an optionally substituted 5 to 7-membered cycloalkyl or cycloalkenyl group; $R^4$ is a hydrogen atom, a hydroxyl group, an -S-glutathione residue, an -S-α-amino acid residue, or an aralkyl group optionally having substituent(s) in the aryl moiety; $R^5$ is a hydrogen atom or a C1–C6 alkyl group, and $R^4$ and $R^5$ may be linked to form a single bond; Y is an oxygen atom or a sulfur atom; n is an integer of from 0 to 5, and the selenium atom may be oxidized.

Inhibitors for restenosis according to the present invention exhibit excellent effect of inhibiting restenosis after PTCA with low toxicity.

BEST MODE FOR CARRYING OUT THE INVENTION

The compounds which are used as active ingredients of inhibitors for restenosis after PTCA according to the present invention are represented by the above-mentioned formula (1) or (1') (hereinafter referred to as compound (1) or (1')). In the formulae, examples of C1–C6 alkyl groups of $R^1$ include methyl, ethyl, propyl, isopropyl, n-butyl, isobutyl, sec-butyl and pentyl; examples of C1-C6 alkoxyl groups of $R^1$ include methoxy, ethoxy and propoxy; examples of aryl groups of $R^3$ include phenyl; examples of cycloalkyl groups of $R^3$ include cyclopentyl, cyclohexyl and cycloheptyl; examples of cycloalkenyl groups of $R^3$ include 1-cyclopentenyl, 1-cyclohexenyl and 1-cycloheptenyl; examples of aromatic heterocyclic groups include 5- or 6-membered aromatic heterocyclic groups such as pyridyl, pyrimidyl, imidazolyl, oxazolyl, isoxazolyl, thiazolyl, furyl, etc. These groups may optionally have substituent(s). Examples of the substituents include a C1–C6 alkyl group, C1–C6 alkoxy group, a halogen atom, a carboxyl group and a hydroxyl group. The number of the substituent(s) is preferably from 1 to 3. Among the mentioned various $R^4$ groups, the -S-glutathione residue is a residue which is formed as a result of elimination of a hydrogen atom from the thiol moiety of glutathione; the -S-α-amino acid residue is a residue which is formed as a result of elimination of a hydrogen atom from the thiol moiety of α-amino acid having a thiol group in the molecule, and examples of the aralkyl group include benzyl. Of these, compounds having $R^4$ and $R^5$ which are linked to form a single bond are preferred, and in particular, 2-phenyl-1,2-benzoisoselenazol-3(2H)-one represented by the following formula is particularly preferred:

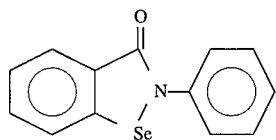

Compounds shown below which are considered to be active metabolites of the above compounds are also useful and encompassed by the present invention.

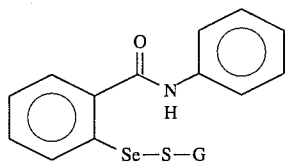

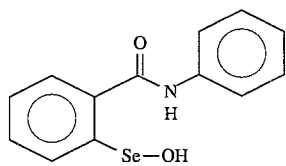

wherein -S-G represents an -S-glutathione group,

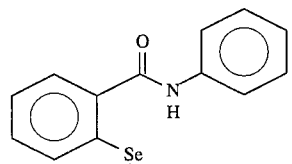

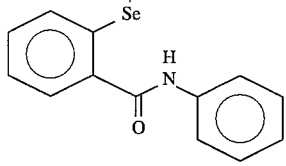

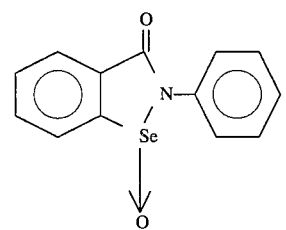

In the present invention, pharmaceutically acceptable salts of the above-described compounds may also be used.

The compounds (1) and (1') are known compounds, and they can be prepared, for example, by methods described in the above-mentioned references.

The compounds (1) and (1'), and their pharmaceutically acceptable salts demonstrated excellent inhibitory effect on the restenosis after PTCA, as will be demonstrated in the test example described below. Regarding the toxicity, the compounds were orally or intraperitoneally administered to mice and rats, and as a result, the compounds were found to have an extremely low toxicity as evidenced by the $LD_{50}$ (mg/kg) values in the following table. High doses of the compounds did not cause any adverse side effects.

TABLE 1

| Animals tested | Administration Route | $LD_{50}$ (mg/kg) |
|---|---|---|
| Mice | p.o. | >6810 |
|  | i.p. | 740 |
| Rats | p.o. | >6810 |
|  | i.p. | 580 |

The restenosis inhibitors of the present invention can be prepared by any methods known per se by adding additives such as lubricants, disintegrators, binders, excipients, etc. to the above-mentioned compounds (1), (1') or their pharmaceutically acceptable salts. They may be formed into oral or parenteral preparations such as tablets, capsules, powders, granules, liquids, suspensions, emulsions, suppositories, etc.

The dose of the compounds (1), (1') or pharmaceutically acceptable salts of (1) or (1') varies depending on the administration route, condition of the patient, etc. In general, it may be from 100 to 2000 mg/day, and especially preferably from 200 to 1000 mg/day for adults in the case of oral administration.

The compounds (1), (1') or the pharmaceutically acceptable salts of (1) or (1') are administered to patients in need of PTCA due to ischemic heart diseases such as angina pectoris. Generally, administration of the compounds starts about three days prior to the operation of PTCA, and continues over a period of three months after the operation. The period in which the compounds are administered after operation may vary according to the condition of the location of the treated part.

EXAMPLE

The present invention will be explained in more detail by the following examples, which, however, should not be construed as limiting the present invention thereto. Test Example:

29 patients suffering from angina pectoris who received elective PTCA (43 sites) orally took 2-phenyl-1,2-benzoisoselenazol-3(2H)-one (hereinafter referred to as compound A) after meal with a daily dose of 200 mg, twice a day, 100 mg for each time, starting from three days prior to the PTCA operation over 3 months after operation (treated group). Coronary angiography was performed before, immediately after and 3 months after PTCA. The stenosed degree was measured by video-densitometry (Reiber JHC et al., *Circulation* 1985; 71:280–288), and inhibition of restenosis was evaluated on the basis of the findings. The results are shown in Table 2.

As control, placebo was given to 50 patients suffering from angina pectoris who received elective PTCA (84 sites) in place of compound A, and coronary angiography was performed before, immediately after and 3 months after PTCA.

In both of the treated and control groups, calcium antagonists such as nifedipine and diltiazem, and antiarteriosclerotic agents such as elastase were concurrently administered as required. As a result, there was no significant difference according to the $\chi^2$ test between the two groups with regard to the use of concomitant compounds and other patient characteristics including the age, the site of the lesion, etc. Accordingly, it is clear that the effect of inhibiting restenosis demonstrated by the group treated with compound A is neither attributed to the sole use of these co-dosed drugs nor to the concomitant therapy by the use of these drugs and compound A.

TABLE 2

| | Time-dependent variation of stenosed degree of post PTCA vessels | | | |
| --- | --- | --- | --- | --- |
| | | Stenosed Degree | | |
| | Number of sites (n) | Before PTCA | After PTCA | 3 Months |
| Control Group | 84 | 87 +/− 11 | 32 +/− 23 | 78 +/− 39 |
| Treated Group | 43 | 89 +/− 10 | 35 +/− 28 | 54 +/− 31* |

(*P<0.05 vs Placebo) Chi square analysis

As apparent from the results in Table 2, the group to which compound A was administered showed a remarkable inhibition of restenosis in the location of operation when compared to the control group. At the point of 6 months after operation, the onset rate of restenosis was 38.2% in the control group while it was 18.6% in the treated group based on the number of patients. Accordingly, the treated group was clinically confirmed to exhibit a higher restenosis inhibitory effect after PTCA than the control group in either evaluation based on the number of lesion sites or that of patients.

Example 1

Tablets:

Tablets each having the following composition were prepared by a method known per se.

| | |
| --- | --- |
| Compound A | 50 mg |
| Carboxymethylcellulose | 25 mg |
| Starch | 5 mg |
| Crystalline Cellulose | 40 mg |
| Magnesium stearate | 2 mg |
| Total | 122 mg |

Industrial Applicability:

The compounds (1), (1') or pharmaceutically acceptable salts of (1) and (1') exhibit excellent inhibitory effect against restenosis after PTCA and less toxicity. Therefore, pharmaceutical agents containing these as active ingredients are useful as an inhibitor for restenosis after PTCA.

We claim:

1. An inhibitor for restenosis after percutaneous coronary arterioplasty, which comprises, as an active ingredient, a compound of the following formula (1), (1') or a pharmaceutically acceptable salt thereof:

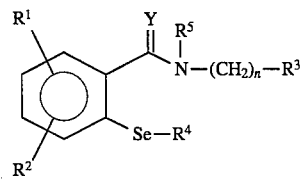

(1)

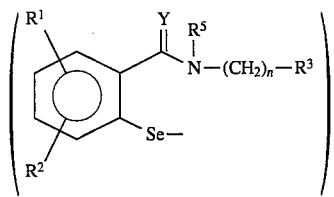

(1')

wherein $R^1$ and $R^2$ are independently a hydrogen atom, a halogen atom, a trifluoromethyl group, a nitro group, a C1–C6 alkyl group or a C1–C6 alkoxyl group, and $R^1$ and $R^2$ may be linked to form a methylenedioxy group; $R^3$ is an optionally substituted aryl group, an optionally substituted aromatic heterocyclic group, an optionally substituted 5 to 7-membered cycloalkyl or cycloalkenyl group; $R^4$ is a hydrogen atom, a hydroxyl group, an -S-glutathione residue, an -S-α-amino acid residue, or an aralkyl group optionally having substituent(s) in the aryl moiety; and $R^5$ is a hydrogen atom or a C1–C6 alkyl group; Y is an oxygen atom or a sulfur atom; n is an integer of from 0 to 5, and the selenium atom may be oxidized.

2. A method of inhibiting restenosis after percutaneous coronary arterioplasty, which comprises:

administering a therapeutically effective amount of a compound of the formula (1), (1') or a pharmaceutically acceptable salt thereof;

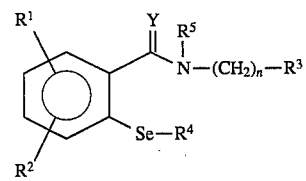

(1)

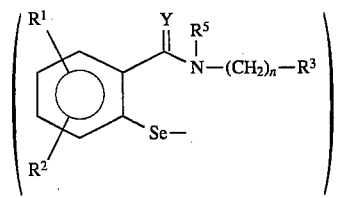

(1')

wherein $R^1$ and $R^2$ are independently a hydrogen atom, a halogen atom, a trifluoromethyl group, a nitro group, a $C_1$14 $C_6$ alkyl group or a $C_1$14 $C_6$ alkoxyl group, and $R^1$ and $R^2$ may be linked to form a methylenedioxy group; $R^3$ is an optionally substituted aryl group, an optionally substituted aromatic heterocyclic group, an optionally substituted 5 to 7-membered cycloalkyl or cycloalkenyl group; $R^4$ is a hydrogen atom, a hydroxyl group, an -S-glutathione residue, an -S-α-amino acid residue, or an aralkyl group optionally having substituent(s) in the aryl moiety; $R^5$ is a hydrogen atom or a $C_1$-$C_6$ alkyl group; and $R^4$ and $R^5$ may be linked to form a single bond; Y is an oxygen atom or a sulfur atom; n is an integer of from 0 to 5, and the selenium atom may be oxidized.

* * * * *